United States Patent [19]
Donovan, Jr.

[11] 4,105,016
[45] Aug. 8, 1978

[54] HEART PUMP

[76] Inventor: Francis M. Donovan, Jr., 6300 Old Canton Rd., Jackson, Miss. 39211

[21] Appl. No.: 742,883

[22] Filed: Nov. 18, 1976

[51] Int. Cl.² .............................................. A61F 1/24
[52] U.S. Cl. ...................................... 128/1 D; 3/1.7; 415/DIG. 4
[58] Field of Search ................... 128/1 D, 214 R, 273; 3/1.7; 415/DIG. 4, 117; 417/373

[56] References Cited
U.S. PATENT DOCUMENTS

| | | | |
|---|---|---|---|
| 3,478,689 | 11/1969 | Ball ........................................ | 417/373 |
| 3,487,784 | 1/1970 | Rafferty et al. ...................... | 3/1.7 X |
| 3,599,244 | 8/1971 | Wortman ............................... | 3/1.7 |
| 3,608,088 | 9/1971 | Dorman et al. ....................... | 3/1.7 |
| 3,842,440 | 11/1974 | Karlson ................................. | 3/1.7 |
| 3,864,055 | 2/1975 | Kletschka et al. ............ | 128/214 R X |

OTHER PUBLICATIONS

Bernstein et al., Trans. Amer. Soc. Artif. Inter. Orgs., vol. XX, 1974, pp. 643-654.

*Primary Examiner*—Dalton L. Truluck
*Attorney, Agent, or Firm*—Anthony DeLaurentis

[57] ABSTRACT

A centrifugal blood pump and method of pumping blood to reduce the pressure in either the right or left ventricle in synchronism with the ventricular contractions of a failing heart. The pump is implanted in a parallel relationship with the ventricle to be assisted and is run at a constant speed. When the pressure in the ventricle reaches a predetermined value, blood will automatically start to flow through the pump thereby reducing the maximum allowable pressure in the ventricle being assisted.

4 Claims, 5 Drawing Figures

HEART PUMP

BACKGROUND OF THE INVENTION

This invention relates to a centrifugal blood pump designed to be used as a cardiac assist device, and the method of using same. More particularly, this invention is an apparatus and method for reducing the maximum pressure in the right or left ventricle of the heart in synchronism with the ventricular contractions.

Centrifugal pumps used to replace or assist a failing heart are known in the prior art. It is particularly important that the natural blood of the heart be maintained. The walls of the vascular system are designed for the particular flow waveform produced by a healthy heart. The blood flow or velocity waveform during each pulsation should be such that there is no breakdown or damage to the blood or the vascular system. Devices presently now in existence either fail to duplicate the pressures and flows that would normally be expected from a healthy heart or require complex control means to establish the desired flow.

One heart assist device uses elaborate sensing means to monitor the pressure in the heart. A complex closed-loop servo-mechanism is used to operate the pump in synchronism to the sensed pressure in the heart and to maintain the programmed stolic pressure.

Another heart assist device simulates the pressure pulsations of a natural heart by either varying the speed of the pump so as to cause the output pressure to change or by running the pump at a constant speed wherein a specially designed diffuser is added to the pump. The diffuser is limited to certain time constants and pulse heights inherent in its design.

SUMMARY OF THE INVENTION

The present invention comprises a method and apparatus used to reduce the maximum pressure which may be obtained in the ventricle of a heart.

A centrifugal pump is placed in a parallel relationship with the ventricle to be assisted. The speed of the pump may be set at the desired speed depending on the wishes of the doctor or patient in accordance with the needs of the patient. As the pressure in the ventricle increases, the pressure across the inlet and outlet of the pump will decrease until, at some predetermined value, blood will commence to flow through the pump thereby limiting the maximum pressure which may be reached in the ventricle. Due to the manner in which the pump operates, the present invention automatically synchronizes itself with the heart and does not interfere with the natural blood flow of the heart.

In the preferred embodiment, the vanes of the pump are logarithmic in shape so as to cause minimum damage to the delicate blood components.

The above and other advantages and features of the present invention will become apparent on making reference to the specification to follow, the drawings and claims.

DESCRIPTION OF THE PREFERRED EMBODIMENT

Figure 1:
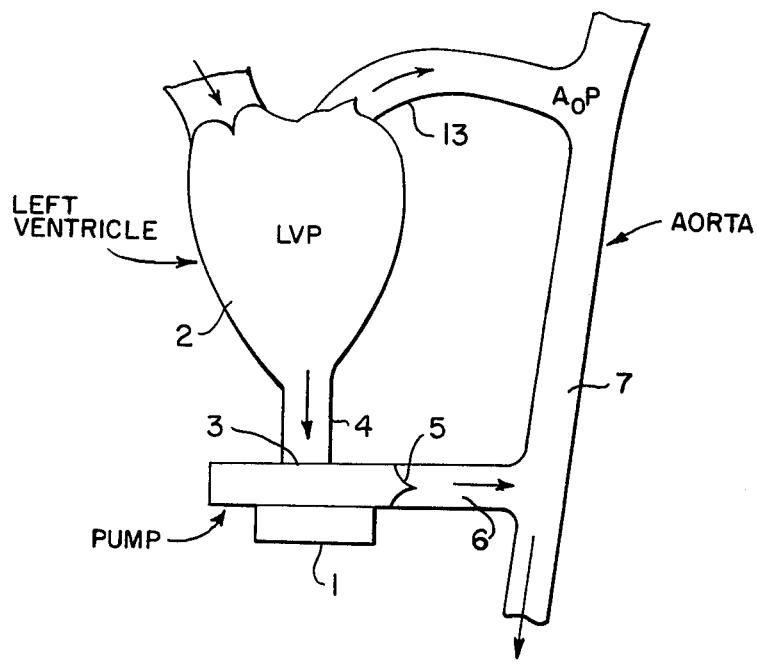
FIG. 1 is a schematic view showing the relationship of the present invention with respect to the ventricle to be assisted and the aorta in which the blood is to be pumped.

Referring to FIG. 1, the preferred embodiment of the present invention is shown comprising a centrifugal pump 1 placed in a parallel relationship with left ventricle of heart 2. Attached to the inlet 3 of pump 1 is cannula 4 which is inserted into the left ventricle of the heart 2. While the preferred embodiment discloses the assistance of the left ventricle, the present invention may be used to assist the right ventricle. Due to the inherent nature of centrifugal pumps, when the pressure difference between the inlet and outlet of the pump decreases fluid will automatically start flowing through the pump. In like manner when the pressure difference across pump 1 reaches a predetermined value, blood will automatically flow through pump 1 through valve 5 into aorta 7. Valve 5 is of the type commonly used for valve replacements.

Figure 2:
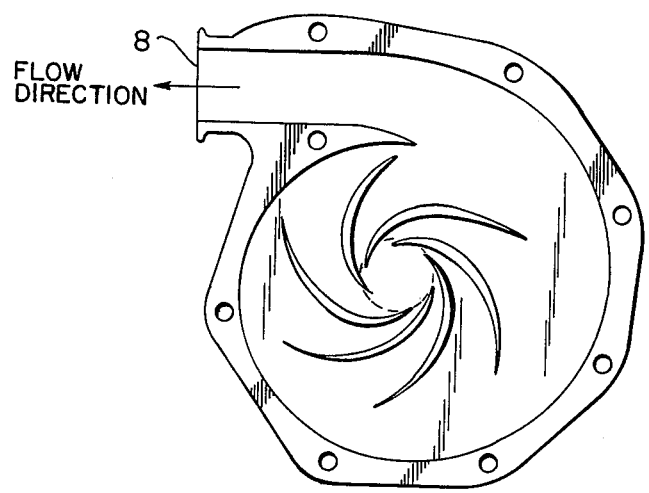
FIG. 2 is a cross-sectional view of the pump of the preferred embodiment showing the logarithmic vanes therein.
Figure 3:
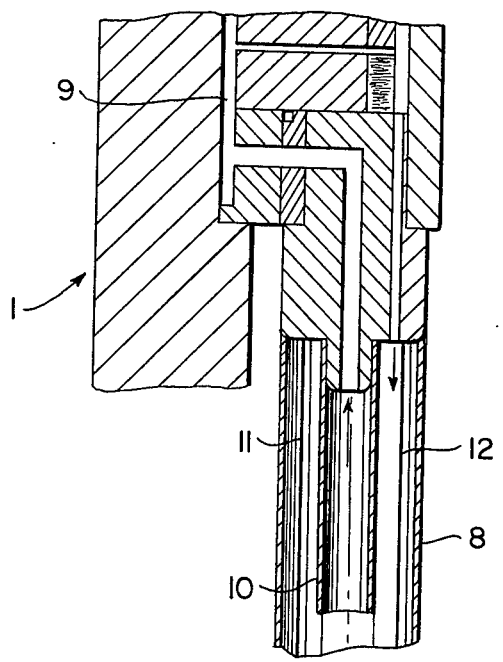
FIG. 3 is a partial side cross-sectional view of the pump of the preferred embodiment showing the cooling and electrical hook-ups.

The pump is constructed of materials which are compatable with body fluids to which they come in contact wherein the pump is implanted. In the preferred embodiment, the vanes of the pump 1 are logarithmic in shape (see FIG. 2) and have a blade angle of 30°. The use of logarithmic vanes will cause a minimum disturbance to the fluid passing through the pump thereby causing a minimal amount of damage to the delicate blood components. Referring to FIG. 3, electrical power and cooling air are supplied to pump 1 by tube 8. Compressed air is carried into the motor chamber 9 by a small inner tube 10. The air enters on one side of the motor, passes over the armature, is collected on the other side of the motor and is conducted back through tube 8 to the atmosphere. Electrical power is carried to the motor by two wires 11 and 12 which pass through the annular space between the tube 8 and inner tube 10. An air flow rate of approximately 10 liters per minute is required to cool the pump 1 when operating under a load. The pump 1 of the preferred embodiment has a constant voltage curve which is very nearly equal to a constant speed curve. As the pressure difference across pump 1 decreases, the flow through pump 1 increases, therefore as the pressure in the ventricle increases, pressure across the inlet 3 and outlet 6 of pump 1 will decrease and will at some predetermined pressure difference commence to pump blood.

Figure 4:
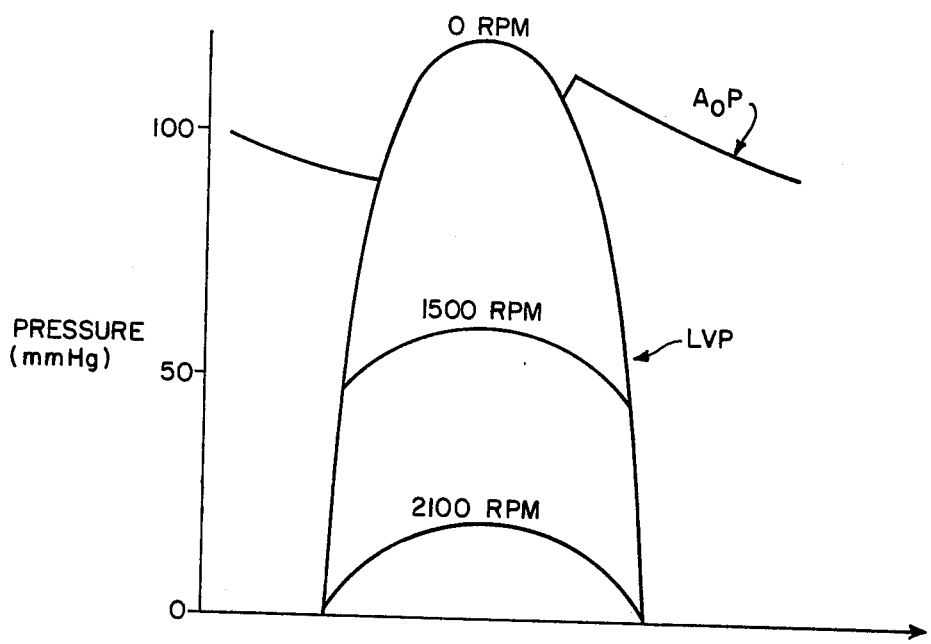
FIG. 4 is a graph illustrating the pressure cycle of a ventricle experiencing failure, and the pressure cycle of the ventricle with the present invention operating at a pump speed of 1,500 rpm and 2,100 rpm, respectively.

The operation of pump 1 at different constant speeds can be understood by referring to FIG. 4. With the pump 1 off or with the by pass not attached to the ventricle, the ventricular pressure curve will have the shape labeled 0 rpm. As the ventricle begins to contract the ventricular pressure increases from approximately 0 mmHg to the end diastolic aorta pressure which is normally about 80 mmHg. At this point, the heart valve 13 of the natural ventricle 2 opens and blood is pumped from the ventricle into the aorta causing the aortic pressure labeled, AOP, to increase to its systolic pressure of 120 mmHg. As the pressure in the left ventricle 2 decreases, the aortic pressure decreases causing outflow valve 13 to close as aortic blood attempts to flow back into the ventricle 2. With pump 1 attached but not running, the valve 5 acts in a fashion similar to valve 13. Under these conditions, the pump 1 has no other effect on the natural system. With pump 1 running at approximately 1,500 rpm, the left ventricle 2 is unable to develop high pressures that occur without the assistance of the present invention. As ventricular pressure increases, the pressure across the pump 1 decreases causing the amount of blood flowing through pump 1 to go from 0 to a relatively large value thereby preventing the built up of pressure in the natural ventricle. If the pump 1 is operated at a higher speed then the maximum pressure which may be reached in the left ventricle decreases even further as shown the curve labeled 2,100 rpm in FIG. 4.

Figure 5:
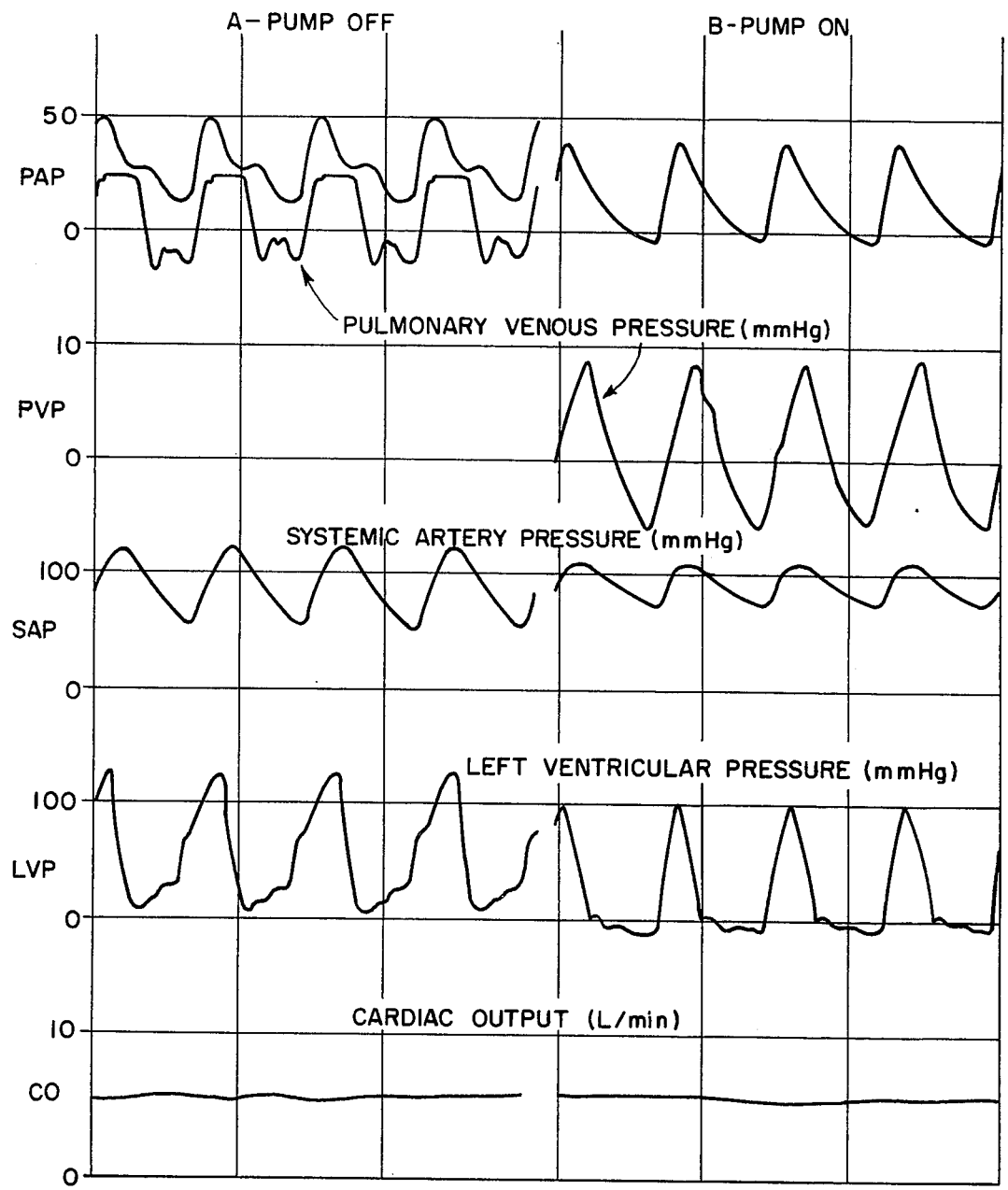
FIG. 5 is a graphic illustration of the pulmonary artery pressure, pulmonary venous pressure, systemic artery pressure, left ventricle pressure and cardiac output of a mock circulatory system with the pump in the on and off states.

A mock circulatory system simulating left ventricle failure produced the data in FIG. 5. During the time period when pump 1 is attached and not running, left ventricular failure is evidenced by the very high pulmonary venous pressure. When the pump 1 is turned on, the symptoms of left ventricular failure disappear. That is, the pulmonary artery pressure decreases to a normal range, the maximum pressure developed in the failing left ventricle decreases, the end diastolic ventricular pressure decreases. It is important to note that no change in cardiac output occurred.

While the methods and forms of apparatus hereindescribed constitute the preferred embodiment of this invention, it is to be understood that changes may be made therein without departing from the scope of the invention which is defined in the appended claims.

I claim:

1. A system for reducing the pressure in the left or right ventrical of a heart pump comprising:
    a centrifugal pump means operated at a constant speed, said pump means having an inlet and an outlet and having a valve means placed in said outlet or inlet, said valve means being of the type commonly used for heart valves;
    a first cannula having one end attached to the inlet of said pump means, the other end of said cannula being adapted to be inserted into the ventricle to be assisted;
    a second cannula having one end attached to the outlet of said pump means, the other end of said second cannula being adapted to be attached to a natural artery;
    a first tube attached to said pump means;
    a second inner tube placed inside of said first tube, said inner tube supplying cooling air to the motor of said pump means, said cooling air being returned to the atmosphere through said first tube; and
    a pair of electrical wires placed in between said second inner tube and said first tube, said wires supplying electrical power to said motor.

2. The system according to claim 1, wherein said centrifugal pump means has logarithmic spiral vanes having a blade angle of 30°.

3. A system for reducing the pressure in the left or right ventricle of a heart comprising:
    a centrifugal pump means operated at a constant speed, said pump means having an inlet and an outlet and having a valve means placed in said outlet or inlet, said valve means being of the type commonly used for heart valves;
    a first cannula having one end attached to the inlet of said pump means, the other end of said cannula being adapted to be inserted in the ventricle to be assisted;
    a second cannula having one end attached to the outlet of said pump means, the other end of said second cannula being adapted to be attached to a natural artery;
    means for supplying electrical power to said pump means;
    a first tube attached to said pump means; and
    a second inner tube placed inside of said first tube, said inner tube supplying cooling air to the motor of said pump means, said cooling air being returned to the atmosphere through said first tube.

4. The system according to claim 3, wherein said means for supplying electrical power to said pump means comprise:
    a pair of electrical wires placed in between said second inner tube and said first tube, said wires supplying the electrical power to said motor.

* * * * *